(12) United States Patent
Palmer

(10) Patent No.: US 10,561,516 B2
(45) Date of Patent: Feb. 18, 2020

(54) REMOVABLE PEDIATRIC HIP ORTHOTIC

(71) Applicant: Jeffrey Ray Palmer, Swisher, IA (US)

(72) Inventor: Jeffrey Ray Palmer, Swisher, IA (US)

( * ) Notice: Subject to any disclaimer, the term of this patent is extended or adjusted under 35 U.S.C. 154(b) by 440 days.

(21) Appl. No.: 15/262,154

(22) Filed: Sep. 12, 2016

(65) Prior Publication Data

US 2018/0071128 A1   Mar. 15, 2018

(51) Int. Cl.
*A61F 5/00* (2006.01)
*A61F 5/01* (2006.01)
*A61F 5/30* (2006.01)
*A61F 5/02* (2006.01)

(52) U.S. Cl.
CPC ............ *A61F 5/0193* (2013.01); *A61F 5/028* (2013.01); *A61F 5/30* (2013.01)

(58) Field of Classification Search
CPC ........ A61F 5/01; A61F 5/0116; A61F 5/0193; A61F 2005/0181; A61F 2005/0183; A61F 2/80
USPC ............................... 602/23, 24; D24/64, 190
See application file for complete search history.

(56) References Cited

U.S. PATENT DOCUMENTS

| | | | | |
|---|---|---|---|---|
| 3,114,368 A | * | 12/1963 | Richmond | A61F 5/0193 602/24 |
| 3,260,259 A | * | 7/1966 | Connelly | A61F 5/0193 602/24 |
| 3,563,601 A | * | 2/1971 | Dickey | A61F 5/0193 280/47.25 |
| 3,730,177 A | * | 5/1973 | Thum | A61F 5/0193 602/24 |
| 3,834,376 A | * | 9/1974 | Thum | A61F 5/0193 602/24 |
| D266,948 S | * | 11/1982 | Kvittingen | A61F 5/0193 D24/190 |
| 4,497,315 A | * | 2/1985 | Fettweis | A61F 5/0193 602/19 |
| 4,964,858 A | * | 10/1990 | Livny | A61F 5/0193 128/DIG. 20 |
| 5,173,979 A | * | 12/1992 | Nennhaus | A61G 7/0755 5/490 |
| 5,267,944 A | * | 12/1993 | Fraser | A61F 5/3784 128/845 |
| 5,618,264 A | * | 4/1997 | Vasquez | A61F 5/0193 602/23 |

(Continued)

OTHER PUBLICATIONS

The University of Iowa Children's Hospital, Hip Spica Cast: A Guide for Patients, publication located on the University of Iowa Children's Hospital website: www.uichildrens.org; dated Feb. 2012.

(Continued)

*Primary Examiner* — Kim M Lewis
(74) *Attorney, Agent, or Firm* — Lane & Waterman LLP; Kathryn E. Cox

(57) ABSTRACT

A removable and replaceable hip orthotic that includes a back panel formed from a rigid material that supports a patient's lumbar area; a front panel formed from the rigid material that supports the patient's abdomen area and is hinged to the back panel to allow application and removal of the orthotic to the patient; a leg support that extends from the back support that includes a space that allows a patient's leg to pass through into the leg support; and straps to secure the back panel to the front panel and the leg into the leg support.

11 Claims, 4 Drawing Sheets

(56) References Cited

U.S. PATENT DOCUMENTS

| | | | | |
|---|---|---|---|---|
| 5,814,001 | A * | 9/1998 | Schwenn | A61F 5/0193 602/23 |
| 6,893,411 | B1 * | 5/2005 | Modglin | A61F 5/0193 128/882 |
| 2012/0109032 | A1 * | 5/2012 | Christenhusz | A61F 5/0193 602/24 |

OTHER PUBLICATIONS

The Royal Children's Hospital Melbourne, Pavlik Harness for DDH, publication located on the Royal Children's Hospital Melbourne website: www.rch.org.au/kidsinfo; dated Nov. 2010.
Cincinnati Children's Hospital Medical Center, Pavlik Harness Care, publication located on the Cincinnati Children's Hospital website: www.cincinnatichildrens.org; dated Mar. 2016.
Becker Orthopedic, Maple Leaf Orthosis, product description sheet located on the Becker Orthopedic website: www.beckerorthopedic.com; dated 2014.
International Hip Dysplasia Institute, Hip Spica Cast—Infant Hip Dysplasia, publication located on the International Hip Dysplasia Institute website: http://hipdysplasia.org.
Restorative Care of America Incorporated, Hip Orthoses, production description sheets located on the Restorative Care of America Incorporated website: www.rcai.com.

* cited by examiner

REMOVABLE PEDIATRIC HIP ORTHOTIC

CROSS-REFERENCE TO RELATED APPLICATION

N/A.

FIELD OF THE INVENTION

The present invention relates to a hip orthotic and, more specifically, to a removable and replaceable pediatric hip orthotic.

BACKGROUND

Developmental dysplasia or dislocation of the hip (DDH) is an abnormal development of the hip joint usually identified in infants and children. In all cases of DDH, the acetabulum (the hip socket) is shallow and the ball of the femur is not stable within the hip socket. However, the severity of DDH can vary from patient to patient. To improve the condition, the hip joint is usually arranged in a position to encourage proper growth for a period of time. Frequently a cast or harness is used to maintain this prescribed position for a period of weeks or months.

The different types of restraints used to keep patients in the therapeutic position vary depending, in part, on the severity of the DDH and the age of the child. One common restraint is the spica cast. The spica cast is a typical hard-sided cast that is generally applied from the waist area to the knees of the patient in an effort to keep the hip joint immobilized in the preferred therapeutic position. Because the spica cast is cumbersome to apply while the patient is in the therapeutic position, the spica cast is typically applied while the patient is under general anesthesia.

Because DDH is often diagnosed and treated in patients that are young and not toilet-trained, special care must be taken when applying the spica cast to allow for diapering of the patient. However, despite the best efforts of parents and caregivers, the spica cast frequently gets soiled with urine and feces. Soiled spica casts can create skin conditions for the patient. A soiled cast that makes contact with the skin can cause rapid skin breakdown leading to discomfort, painful sores, rashes, and other skin conditions. Because the spica cast is generally worn for 6 to 12 weeks at a time, the child must either be left in a soiled cast which may cause skin irritation or have a new cast applied which may require general anesthetic. It is desirable therefore, to have a cast that can be removed and cleaned or replaced when soiled but that does not require anesthesia or significant discomfort to the patient during removal and re-application.

SUMMARY

In one aspect, a removable and replaceable rigid hip orthotic is disclosed comprising a back panel configured to support a patient's lower back area; a front panel configured to support a patient's lower abdominal area that is attached to the back panel via a hinge that allows the front panel to rotate; and a leg support configured to support a patient's leg, thereby placing the hip joint in a therapeutic position. In one embodiment the leg support includes a gap or space to allow the patients leg to pass through and be received by the leg support allowing the orthotic to be removable and replaceable. The orthotic is secured to the patient with straps around the lumbar-abdominal region and around the leg supports.

In another aspect, a layer of padding is added to the inside of the orthotic between the patient and the rigid orthotic to provide cushioning. In one embodiment the padding is removable from the orthotic to allow replacement of the padding.

In certain embodiments, the straps are locked to prevent removal of the orthotic without medical supervision. In one embodiment, a Boa dial is used to lock the straps in place.

The above described features and advantages, as well as others, will become more readily apparent to those of ordinary skill in the art by reference to the following detailed description and accompanying drawings. While it would be desirable to provide an orthotic that includes one or more of these advantageous features, the teachings disclosed herein extend to those embodiments which fall within the scope of the appended claims, regardless of whether they accomplish one or more of the above-mentioned advantages.

DETAILED DESCRIPTION

Figure 1:
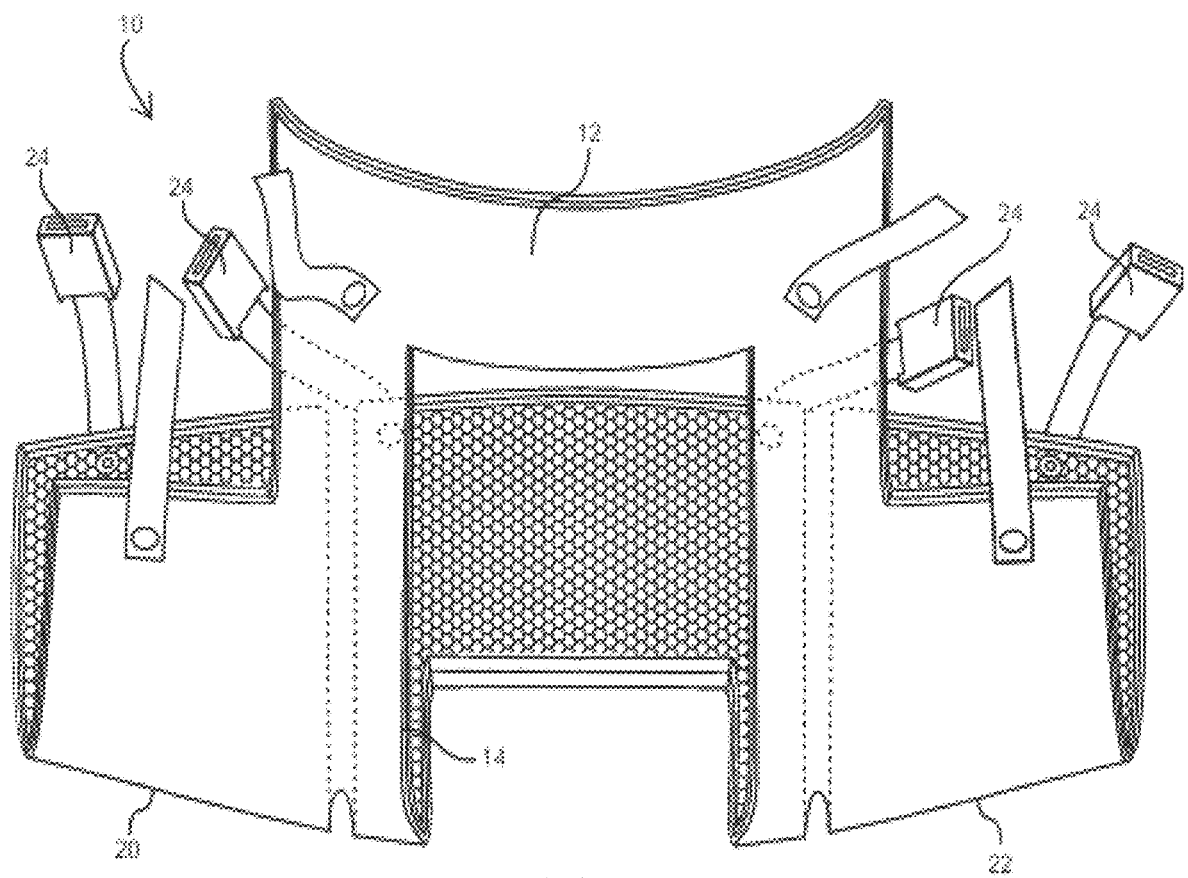
FIG. 1 is a posterior view of the orthotic.

For the purposes of promoting an understanding of the principles of the invention, reference will now be made to the embodiments illustrated in the drawings and described in the following written specification. It is understood that no limitation to the scope of the invention is thereby intended. It is further understood that the present invention includes any alterations and modifications to the illustrated embodiments and includes further applications of the principles of the invention as would normally occur to one skilled in the art to which this invention pertains.

One type of hip orthotic 10 is shown in FIG. 1. The orthotic 10 includes a back panel 12 which is molded to fit the lower back/lumbar sacral area of the patient and which contours around the patient's back and laterally to provide stability and structural integrity of the orthotic 10. The back panel 12 is formed from polypropylene or any other suitable material that is heat-formable and waterproof, but is generally rigid in construction so as to support the patient in the therapeutic position. It further includes an aperture 14 to reduce the amount of skin covered by the orthotic 10 and to allow access to the diaper area of the patient. It can be understood that the aperture 14 can be of varying size and shape but must remain limited in some respects to ensure structural stability of the orthotic 10.

Figure 2:
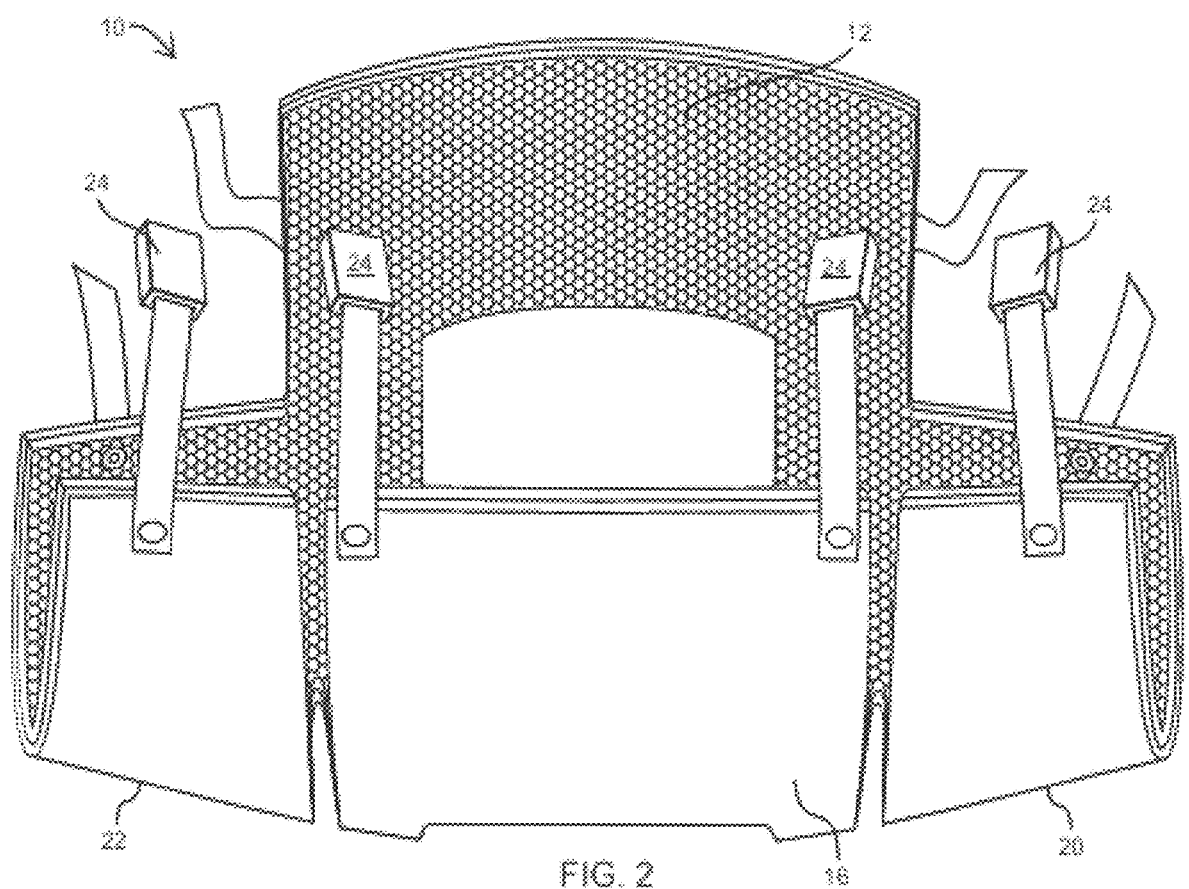
FIG. 2 is an anterior view of the orthotic shown in FIG. 1.
Figure 3:
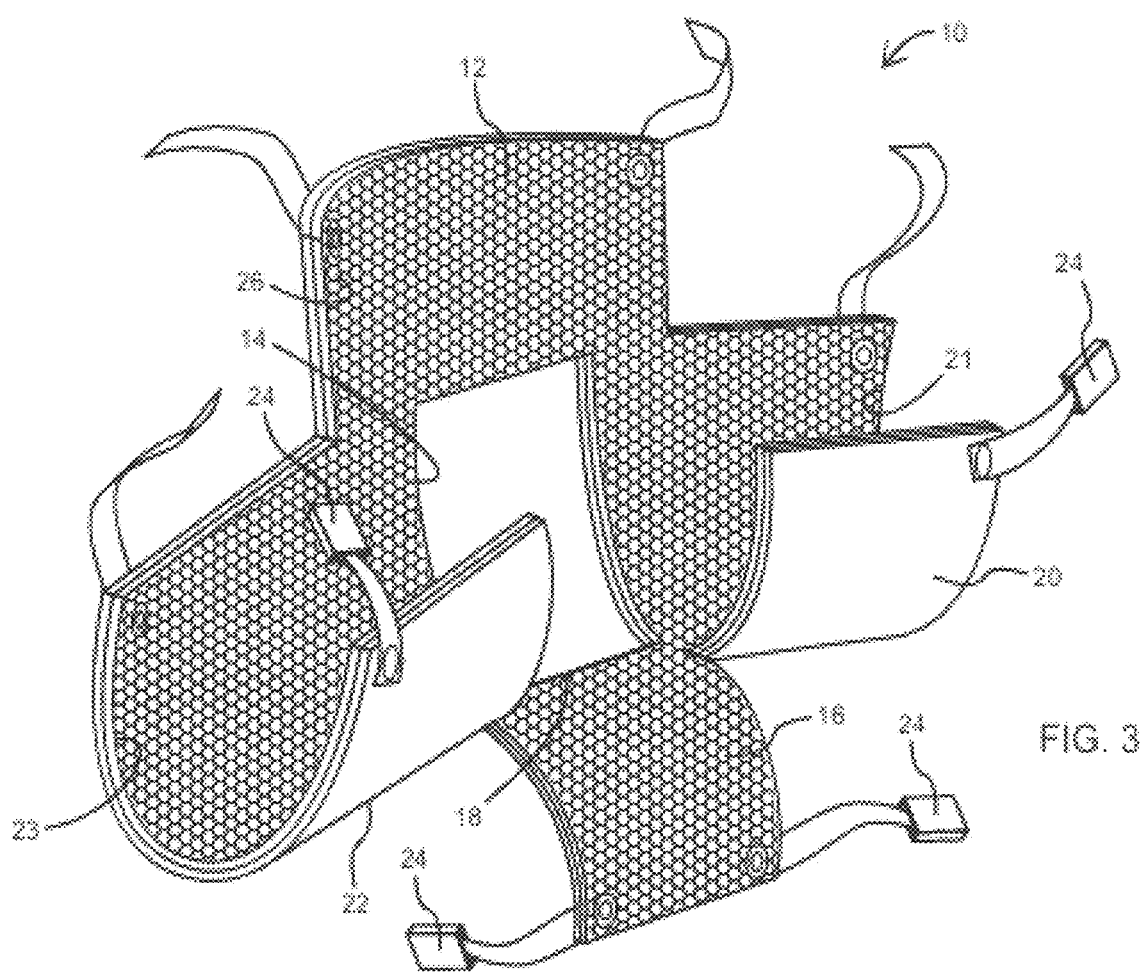
FIG. 3 is a perspective view of the orthotic shown in FIG. 1.

The orthotic 10 also includes a front panel 16 as best shown in FIG. 2. The front panel 16 can be formed from the same rigid polypropylene material as the back panel 12 and can be formed as a part of a unitary construction with the back panel 12. In one embodiment, the front panel 16 is movable with respect to the back panel 12 via a hinge 18 (best shown in FIG. 3). The hinge 18 can be any type of hinge that allows the front panel 16 to move or rotate with respect to the back panel 12. In one embodiment, the front panel 16 is scored to form the hinge 18 but other types of hinges are contemplated by this disclosure. As those with skill in the art can appreciate, the hinged front panel 16 allows the orthotic 10 to be applied and removed from the patient more easily. Additionally, the hinged front panel 16 allows for additional diaper area access if necessary.

Figure 4:
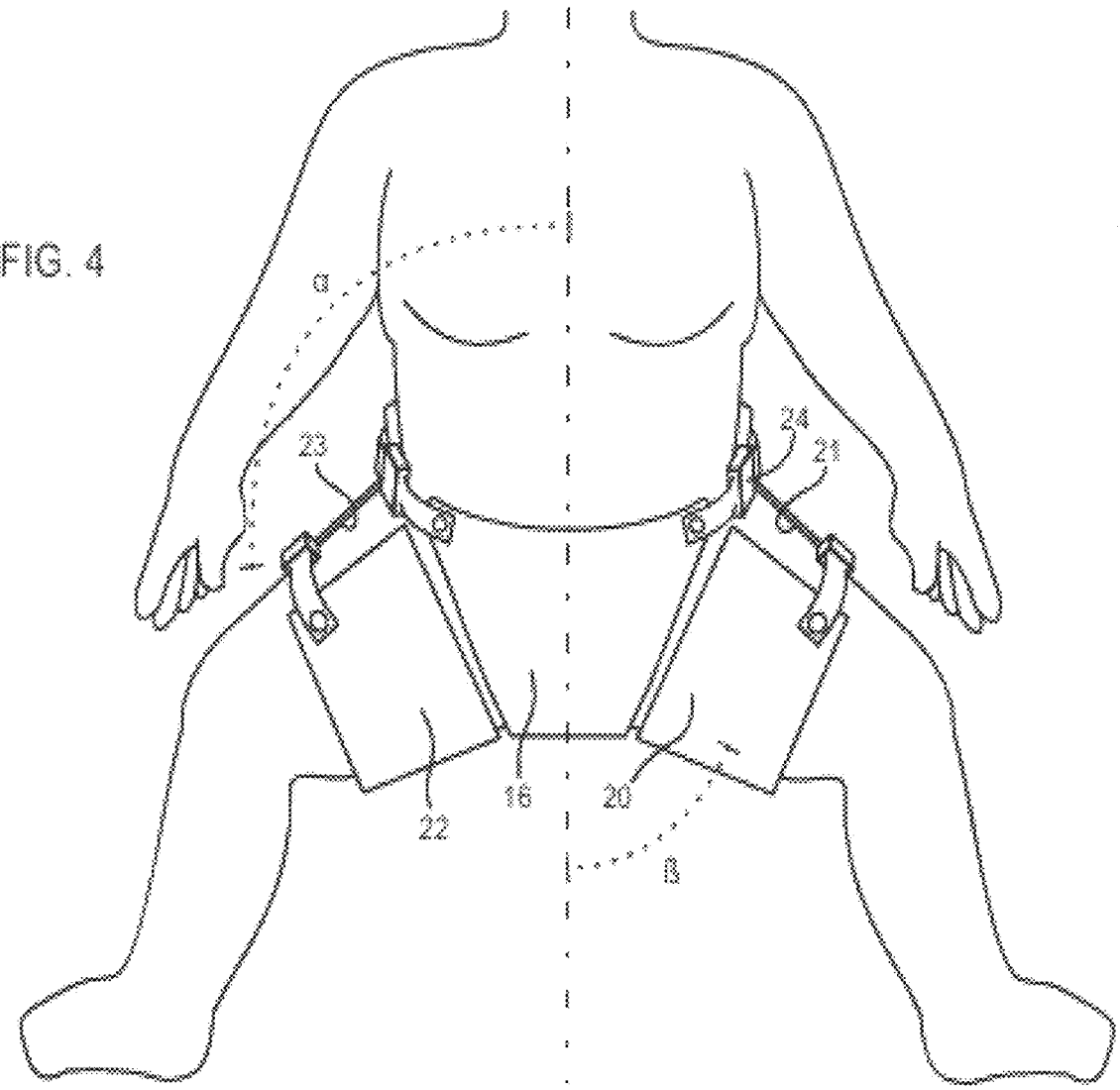
FIG. 4 is an anterior view of the orthotic shown in FIG. 1 as applied to a patient.

The orthotic 10 also includes a left leg support 20 and a right leg support 22 though it can be understood that if only one hip joint is affected by DDH, only one of the leg supports may be necessary. The leg supports 20, 22 are similarly formed out of a generally rigid material such as polypropylene, and can be formed in a unitary construction with the back panel 12 and front panel 16 as shown in one embodiment. The leg supports 20, 22 are positioned in such a way as to hold the patient's legs in the prescribed therapeutic position. The leg supports 20, 22 include openings 21, 23 which allow for the patient's legs to be moved into the orthotic 10. The openings 21, 23 are sized to allow the patient's leg to pass through into the orthotic 10. The leg supports 20, 22, when used to treat DDH, generally hold the patient's legs in a therapeutic position of which two angles are of particular importance, the angle of abduction $\alpha$ and the angle of flexion $\beta$. In most cases of DDH, the prescribed position is 45 degrees abduction $\alpha$, and between 90 and 100 degrees flexion $\beta$ as best shown in FIG. 4. It should be understood however, that this orthotic 10 can be used for various leg support angles, not just those associated with DDH.

It can be appreciated that the orthotic 10 can be either be molded to the individual patient or prefabricated in a variety of different sizes to accommodate a multitude of patients. Patients can be measured or scanned to collect size information for the orthotic 10 and then fitted with the appropriately sized orthotic 10. When the orthotic 10 is applied to the patient, the patient will not generally need to be anesthetized. The front panel 16 can be opened at the hinge 18 to accommodate placement of the orthotic 10 and the legs of the patient can pass through openings 21, 23 in the leg supports 20, 22. Once the patient is positioned in the orthotic 10, straps 24 can be used to firmly but comfortably hold the orthotic 10 in place. In one embodiment, straps 24 are used around the lumbar region, on each leg support 20, 22 and to secure the front panel 16 to the back panel 12. The straps 24 can be hook and loop fasteners, or use buckle fasteners, snaps, or any other suitable means for firmly holding the orthotic 10 in place. Such straps may also have locking features, such as a Boa dial to prevent the removal of the orthotic 10 without supervision or assistance.

The orthotic 10 can also include a removable padding layer 26 as best shown in FIG. 2. The padding 26 can be a soft foam or other suitable material that can provide a barrier layer between the orthotic 10 and the patient. The padding 26 provides an element of comfort for the orthotic 10, but also increases the hygiene of the orthotic 10 as the orthotic 10 can be removed and the padding 26 either replaced or cleaned in the event of fecal/urine contamination. It can be appreciated that the padding layer 26 can reduce the discomfort of the patient and reduce skin irritations from the orthotic 10. Moreover, it can be appreciated that the orthotic 10 can be worn without the padding 26 while the patient bathes.

It should be understood that this disclosure is, in many respects, only illustrative. Changes may be made in details, particularly in matters of shape, and size without exceeding the scope of the invention. The invention's scope is, of course, defined in the language in which the appended claims are expressed.

What is claimed is:

1. An orthotic comprising:
   a back panel formed of a rigid material and configured to support a patient's lumbar region;
   a front panel formed of the rigid material and configured to support the patient's lower abdomen region, wherein the front panel is attached to the back panel via a hinge and the front panel is at least partially rotatable about the hinge, and wherein the front panel, when in a first position, can be secured to the back panel around the patient with at least one strap and when in a second position, can accommodate the removal and application of the orthotic to a patient; and
   at least one leg support, configured to support a patient's leg in a therapeutic position wherein the leg support is formed from the rigid material that extends from a lateral edge of the back panel and further comprises a gap that extends from a proximal end of the leg support to a distal end of the leg support wherein the patient's leg can pass through the gap into the leg support and can be secured in place by at least one strap.

2. The orthotic of claim 1, wherein the orthotic further comprises a layer of padding that extends along an inside surface of the orthotic, wherein the padding layer is removable from the orthotic.

3. The orthotic of claim 1, wherein the back panel further comprises an aperture located generally in a patient's diaper area wherein the aperture is configured to allow diapering of the patient.

4. The orthotic of claim 1, wherein the at least one strap include locks, wherein the locks prevent the at least one strap from coming unsecured.

5. The orthotic of claim 1, wherein the hinge is comprised of a scored line in the rigid material.

6. A removable and replaceable pediatric hip orthotic comprising: an abdominal support having a front panel configured to rigidly support a patient's abdomen, and a back panel configured to rigidly support a patient's lower back and sides, wherein the front panel and back panel can be secured together with a strap when the front panel is in a first position and wherein the front panel can be moved to a second position to accommodate removal of the orthotic; and
   at least one leg support, configured to rigidly support a patient's hip joint in a therapeutic position, wherein the leg support is attached to the back panel and includes a slot extending from the back panel to a distal end of the at least one leg support to accommodate removal and application of the orthotic.

7. The orthotic of claim 6, further comprising a padding layer that extends across an inside surface of the orthotic, wherein the padding layer is removable from the orthotic.

8. The orthotic of claim 7, wherein the back panel further comprises an aperture to allow access to a patient's diaper area.

9. The orthotic of claim 8, wherein there are two leg supports.

10. The orthotic of claim 6, wherein the strap further comprises locks that keep the strap secure.

11. The orthotic of claim 6, wherein the front panel is scored to allow movement between the first position and the second position.

* * * * *